(12) United States Patent
Brazzini et al.

(10) Patent No.: US 8,192,455 B2
(45) Date of Patent: Jun. 5, 2012

(54) COMPRESSIVE DEVICE FOR PERCUTANEOUS TREATMENT OF OBESITY

(75) Inventors: Augusto Brazzini, New Orleans, LA (US); David S. Kirsch, Jefferson, LA (US); Wilfrido R. Castaneda-Zuniga, New Orleans, LA (US); Horacio D'Agostino, Shreveport, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 1629 days.

(21) Appl. No.: 10/567,199

(22) PCT Filed: Jul. 30, 2004

(86) PCT No.: PCT/US2004/024612
§ 371 (c)(1),
(2), (4) Date: Aug. 14, 2006

(87) PCT Pub. No.: WO2005/018417
PCT Pub. Date: Mar. 3, 2005

(65) Prior Publication Data
US 2007/0060940 A1    Mar. 15, 2007

Related U.S. Application Data

(60) Provisional application No. 60/494,698, filed on Aug. 13, 2003.

(51) Int. Cl.
*A61M 29/00*    (2006.01)
(52) U.S. Cl. ............ 606/192; 606/191; 600/37; 128/898

(58) Field of Classification Search .................... 600/37; 606/191, 192, 195; 128/898
See application file for complete search history.

(56) References Cited

U.S. PATENT DOCUMENTS
233,475 A    10/1880    Cook et al.
(Continued)

FOREIGN PATENT DOCUMENTS
EP    1 016 377 A2    7/2000
(Continued)

OTHER PUBLICATIONS

Brolin, R.E., "Gastric Bypass," *Surg. Clinics of North America*, vol. 81(5), pp. 1077-1096 (2001).

(Continued)

*Primary Examiner* — Gary Jackson
*Assistant Examiner* — Michael Mendoza
(74) *Attorney, Agent, or Firm* — Alan W. Cannon

(57) ABSTRACT

An apparatus and method for treating morbid obesity in mammals using a gastric reduction assembly that reduces the gastric volume of a stomach and induces early satiety. The gastric reduction assembly comprises at least two or more expandable devices, each able to be adjustably inflated with a fluid (e.g., a liquid or a gas) using a filling tube. In a preferred embodiment, the gastric reduction assembly is inserted through the abdominal wall and placed at a location exterior to the stomach body, avoiding an abdominal incision. Once positioned near the stomach body, the gastric reduction assembly allows for the external compression of the stomach body to limit food intake. The gastric reduction assembly also minimizes the potential for shifting of the expandable devices after insertion to the stomach body to revert to its pre-compressed state.

8 Claims, 3 Drawing Sheets

U.S. PATENT DOCUMENTS

| | | | |
|---|---|---|---|
| 659,422 A | 10/1900 | Shidler | |
| 780,392 A | 1/1905 | Wanamaker et al. | |
| 789,467 A | 5/1905 | West | |
| 1,461,524 A | 7/1923 | Goddard | |
| 2,579,192 A | 12/1951 | Kohl et al. | |
| 2,646,298 A | 7/1953 | Leary | |
| 2,697,624 A | 12/1954 | Thomas et al. | |
| 2,734,299 A | 2/1956 | Masson | |
| 2,825,592 A | 3/1958 | Semple | |
| 3,326,586 A | 6/1967 | Frost et al. | |
| 3,470,834 A | 10/1969 | Bone | |
| 3,521,918 A | 7/1970 | Hammond | |
| 3,571,864 A | 3/1971 | Emile et al. | |
| 3,664,435 A | 5/1972 | Klessig | |
| 3,675,639 A | 7/1972 | Climber | |
| 3,713,680 A | 1/1973 | Pagano | |
| 3,756,638 A | 9/1973 | Stockberger | |
| 3,873,140 A | 3/1975 | Bloch | |
| 3,931,667 A | 1/1976 | Merser et al. | |
| 3,976,079 A | 8/1976 | Samuels et al. | |
| 4,006,747 A | 2/1977 | Kronenthal et al. | |
| 4,060,089 A | 11/1977 | Noiles | |
| 4,133,315 A | 1/1979 | Berman et al. | |
| 4,210,148 A | 7/1980 | Stivala | |
| 4,246,893 A | 1/1981 | Berson | 128/1 R |
| 4,291,698 A | 9/1981 | Fuchs et al. | |
| 4,328,805 A | 5/1982 | Akopov et al. | |
| 4,416,267 A | 11/1983 | Garren et al. | |
| 4,458,681 A | 7/1984 | Hopkins | |
| 4,472,226 A | 9/1984 | Redinger et al. | |
| 4,485,805 A | 12/1984 | Foster, Jr. et al. | |
| 4,493,323 A | 1/1985 | Albright et al. | |
| 4,558,699 A | 12/1985 | Bashour | |
| 4,592,339 A | 6/1986 | Kuzmak et al. | |
| 4,592,342 A | 6/1986 | Salmasian | |
| 4,621,640 A | 11/1986 | Mulhollan et al. | |
| 4,669,473 A | 6/1987 | Richards et al. | |
| 4,694,827 A | 9/1987 | Weiner et al. | 128/303 R |
| 4,696,288 A | 9/1987 | Kuzmak et al. | |
| 4,705,040 A | 11/1987 | Mueller et al. | |
| 4,714,281 A | 12/1987 | Peck | |
| 4,723,547 A | 2/1988 | Kullas et al. | |
| 4,738,255 A | 4/1988 | Goble et al. | |
| 4,739,758 A | 4/1988 | Lai et al. | |
| 4,744,364 A | 5/1988 | Kensey | |
| 4,750,492 A | 6/1988 | Jacobs | |
| 4,803,985 A | 2/1989 | Hill | |
| 4,823,794 A | 4/1989 | Pierce | |
| 4,899,747 A | 2/1990 | Garren et al. | |
| 4,955,913 A | 9/1990 | Robinson | |
| 5,002,550 A | 3/1991 | Li | |
| 5,033,481 A | 7/1991 | Heyler, III | |
| 5,041,129 A | 8/1991 | Hayhurst et al. | |
| 5,084,061 A | 1/1992 | Gau et al. | |
| 5,100,421 A | 3/1992 | Christoudias | |
| 5,112,310 A * | 5/1992 | Grobe | 604/175 |
| 5,123,914 A | 6/1992 | Cope | |
| 5,129,912 A | 7/1992 | Noda et al. | |
| RE34,021 E | 8/1992 | Mueller et al. | |
| 5,151,086 A * | 9/1992 | Duh et al. | 604/506 |
| 5,188,104 A | 2/1993 | Wernicke et al. | |
| 5,217,470 A | 6/1993 | Weston | |
| 5,234,454 A | 8/1993 | Bangs | 606/191 |
| 5,246,456 A | 9/1993 | Wilkinson | |
| 5,258,015 A | 11/1993 | Li et al. | |
| 5,259,399 A | 11/1993 | Brown | |
| 5,269,809 A | 12/1993 | Hayhurst et al. | |
| 5,292,344 A | 3/1994 | Douglas | |
| 5,334,200 A | 8/1994 | Johnson | |
| 5,354,271 A | 10/1994 | Voda | |
| 5,364,408 A | 11/1994 | Gordon | |
| 5,391,182 A | 2/1995 | Chin | |
| 5,405,352 A | 4/1995 | Weston | |
| 5,423,872 A | 6/1995 | Cigaina | |
| 5,428,123 A | 6/1995 | Ward et al. | |
| 5,445,608 A | 8/1995 | Chen et al. | |
| 5,470,337 A | 11/1995 | Moss | |
| 5,472,446 A | 12/1995 | Torre | |
| 5,480,406 A | 1/1996 | Nolan et al. | |
| 5,496,311 A | 3/1996 | Abele et al. | |
| 5,507,754 A | 4/1996 | Green et al. | |
| 5,545,171 A | 8/1996 | Sharkey et al. | |
| 5,545,178 A | 8/1996 | Kensey et al. | |
| 5,549,621 A | 8/1996 | Bessler et al. | |
| 5,554,162 A | 9/1996 | DeLange | |
| 5,573,540 A | 11/1996 | Yoon | |
| 5,591,177 A | 1/1997 | Lehrer | |
| 5,601,604 A | 2/1997 | Vincent | |
| 5,626,614 A | 5/1997 | Hart | |
| 5,634,936 A | 6/1997 | Linden et al. | |
| 5,647,836 A | 7/1997 | Blake, III et al. | |
| 5,690,691 A | 11/1997 | Chen et al. | |
| 5,716,368 A | 2/1998 | Torre et al. | |
| 5,725,557 A | 3/1998 | Gatturna et al. | |
| 5,846,254 A | 12/1998 | Schulze et al. | |
| 5,888,196 A | 3/1999 | Bonutti | |
| 5,931,788 A | 8/1999 | Keen et al. | |
| 5,938,669 A | 8/1999 | Klaiber et al. | |
| 5,951,590 A | 9/1999 | Goldfarb | |
| 5,961,440 A | 10/1999 | Schweich, Jr. et al. | |
| 5,971,447 A | 10/1999 | Steck, III | |
| 5,993,473 A | 11/1999 | Chan et al. | 606/192 |
| 6,013,053 A | 1/2000 | Bower et al. | |
| 6,067,991 A | 5/2000 | Forsell | |
| 6,080,160 A | 6/2000 | Chen et al. | |
| 6,097,984 A | 8/2000 | Douglas | |
| 6,102,922 A | 8/2000 | Jakobsson et al. | 606/157 |
| 6,113,609 A | 9/2000 | Adams | |
| 6,143,006 A | 11/2000 | Chan | |
| 6,162,234 A | 12/2000 | Freedland et al. | |
| 6,186,149 B1 | 2/2001 | Pacella et al. | |
| 6,270,530 B1 | 8/2001 | Eldridge et al. | |
| 6,420,452 B1 | 7/2002 | Gunatillake et al. | |
| 6,437,073 B1 | 8/2002 | Gunatillake et al. | |
| 6,447,533 B1 | 9/2002 | Adams | |
| 6,454,785 B2 | 9/2002 | De Hoyos Garza | |
| 6,475,136 B1 | 11/2002 | Forsell | 600/37 |
| 6,488,691 B1 | 12/2002 | Carroll et al. | |
| 6,491,707 B2 | 12/2002 | Makower et al. | |
| 6,494,888 B1 | 12/2002 | Laufer et al. | |
| 6,500,148 B1 | 12/2002 | Pinchuk et al. | |
| 6,506,196 B1 | 1/2003 | Laufer | |
| 6,511,490 B2 | 1/2003 | Robert | 606/151 |
| 6,535,764 B2 | 3/2003 | Imran et al. | |
| 6,558,400 B2 | 5/2003 | Deem et al. | |
| 6,656,182 B1 | 12/2003 | Hayhurst | |
| 6,663,639 B1 | 12/2003 | Laufer et al. | |
| 6,669,713 B2 | 12/2003 | Adams | |
| 6,675,809 B2 | 1/2004 | Stack et al. | |
| 6,736,793 B2 | 5/2004 | Meyer et al. | |
| 6,746,460 B2 | 6/2004 | Gannoe et al. | |
| 6,755,869 B2 | 6/2004 | Geitz | |
| 6,773,441 B1 | 8/2004 | Laufer et al. | |
| 6,790,213 B2 | 9/2004 | Cherok et al. | |
| 6,821,285 B2 | 11/2004 | Laufer et al. | |
| 6,835,200 B2 | 12/2004 | Laufer et al. | |
| 6,869,395 B2 | 3/2005 | Page et al. | |
| 6,900,055 B1 | 5/2005 | Fuller | |
| 6,908,487 B2 | 6/2005 | Cigaina | |
| 6,981,978 B2 | 1/2006 | Gannoe | |
| 6,994,715 B2 | 2/2006 | Gannoe et al. | |
| 7,033,373 B2 | 4/2006 | de la Torre et al. | |
| 7,037,344 B2 | 5/2006 | Kagan et al. | |
| 7,153,314 B2 | 12/2006 | Laufer et al. | |
| 7,167,750 B2 | 1/2007 | Knudson et al. | |
| 7,223,277 B2 | 5/2007 | DeLegge | |
| 7,255,675 B2 | 8/2007 | Gertner et al. | |
| 7,338,433 B2 | 3/2008 | Coe | |
| 7,354,454 B2 | 4/2008 | Stack et al. | |
| 7,374,565 B2 | 5/2008 | Hassler et al. | |
| 7,402,166 B2 | 7/2008 | Feigl | |
| 7,416,554 B2 | 8/2008 | Lam et al. | |
| 7,618,426 B2 | 11/2009 | Ewers et al. | |
| 7,666,195 B2 | 2/2010 | Kelleher et al. | |
| 7,670,279 B2 | 3/2010 | Gertner | |
| 7,841,978 B2 | 11/2010 | Gertner | |
| 7,862,546 B2 | 1/2011 | Conlon et al. | |

| | | |
|---|---|---|
| 7,988,617 B2 | 8/2011 | Gertner |
| 2001/0010005 A1 | 7/2001 | Kammerer et al. |
| 2001/0011543 A1 | 8/2001 | Forsell |
| 2001/0044639 A1 | 11/2001 | Levinson |
| 2002/0055757 A1 | 5/2002 | Torre et al. |
| 2002/0128684 A1 | 9/2002 | Foerster |
| 2002/0161382 A1 | 10/2002 | Neisz et al. |
| 2002/0161414 A1 | 10/2002 | Flesler et al. |
| 2002/0188354 A1 | 12/2002 | Peghini ............... 623/23.65 |
| 2003/0021822 A1 | 1/2003 | Lloyd |
| 2003/0055463 A1 | 3/2003 | Gordon et al. |
| 2003/0055465 A1 | 3/2003 | Ben-Haim et al. |
| 2003/0093117 A1 | 5/2003 | Saadat |
| 2003/0208212 A1 | 11/2003 | Cigaina |
| 2004/0006351 A1 | 1/2004 | Gannoe et al. |
| 2004/0024386 A1 | 2/2004 | Deem et al. |
| 2004/0030347 A1 | 2/2004 | Gannoe |
| 2004/0044353 A1 | 3/2004 | Gannoe |
| 2004/0044357 A1 | 3/2004 | Gannoe |
| 2004/0054352 A1 | 3/2004 | Adams et al. |
| 2004/0059289 A1 | 3/2004 | Garza Alvarez |
| 2004/0068224 A1 | 4/2004 | Couvillon et al. |
| 2004/0092892 A1 | 5/2004 | Kagan et al. |
| 2004/0097986 A1 | 5/2004 | Adams |
| 2004/0098060 A1 | 5/2004 | Ternes |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0148034 A1 | 7/2004 | Kagan et al. |
| 2004/0186503 A1 | 9/2004 | Delegge |
| 2004/0193194 A1 | 9/2004 | Laufer et al. |
| 2004/0194790 A1 | 10/2004 | Laufer et al. |
| 2004/0243178 A1 | 12/2004 | Haut et al. |
| 2004/0243179 A1 | 12/2004 | Foerster |
| 2004/0243180 A1 | 12/2004 | Donnelly et al. |
| 2004/0260345 A1 | 12/2004 | Foerster |
| 2004/0267378 A1 | 12/2004 | Gazi et al. |
| 2005/0022827 A1 | 2/2005 | Woo et al. |
| 2005/0049718 A1 | 3/2005 | Dann et al. |
| 2005/0159769 A1 | 7/2005 | Alverdy |
| 2005/0197687 A1 | 9/2005 | Molaei et al. |
| 2005/0203344 A1 | 9/2005 | Orban, III et al. |
| 2005/0216040 A1 | 9/2005 | Gertner et al. |
| 2005/0216042 A1 | 9/2005 | Gertner et al. |
| 2005/0228415 A1 | 10/2005 | Gertner |
| 2005/0261712 A1 | 11/2005 | Balbierz |
| 2005/0267405 A1 | 12/2005 | Shah |
| 2005/0267406 A1 | 12/2005 | Hassler, Jr. |
| 2005/0267533 A1 | 12/2005 | Gertner |
| 2005/0267595 A1 | 12/2005 | Chen et al. |
| 2005/0267596 A1 | 12/2005 | Chen et al. |
| 2005/0277960 A1 | 12/2005 | Hassler, Jr. et al. |
| 2005/0277974 A1 | 12/2005 | Hassler, Jr. et al. |
| 2006/0009789 A1 | 1/2006 | Gambale et al. |
| 2006/0025789 A1 | 2/2006 | Laufer et al. |
| 2006/0058829 A1 | 3/2006 | Sampson |
| 2006/0089571 A1 | 4/2006 | Gertner |
| 2006/0106288 A1 | 5/2006 | Roth et al. |
| 2006/0161186 A1 | 7/2006 | Hassler, Jr. et al. |
| 2006/0161256 A1 | 7/2006 | Ziegler et al. |
| 2006/0195139 A1 | 8/2006 | Gertner |
| 2006/0212053 A1 | 9/2006 | Gertner |
| 2006/0253131 A1 | 11/2006 | Wolniewicz |
| 2006/0264699 A1 | 11/2006 | Gertner |
| 2007/0027358 A1 | 2/2007 | Gertner et al. |
| 2007/0060940 A1 | 3/2007 | Brazzini et al. |
| 2007/0073318 A1 | 3/2007 | Carter et al. |
| 2007/0073323 A1 | 3/2007 | Carter et al. |
| 2007/0088373 A1 | 4/2007 | Baker |
| 2007/0112363 A1 | 5/2007 | Adams |
| 2007/0129738 A1 | 6/2007 | Kraemer et al. |
| 2007/0167982 A1 | 7/2007 | Gertner et al. |
| 2007/0173869 A1 | 7/2007 | Gannoe et al. |
| 2007/0173888 A1 | 7/2007 | Gertner et al. |
| 2007/0179335 A1 | 8/2007 | Gertner et al. |
| 2007/0203517 A1 | 8/2007 | Williams et al. |
| 2007/0233170 A1 | 10/2007 | Gertner, et al. |
| 2007/0235083 A1 | 10/2007 | Dlugos |
| 2007/0239284 A1 | 10/2007 | Skerven et al. |
| 2007/0250103 A1 | 10/2007 | Makower |
| 2007/0255308 A1 | 11/2007 | Williams et al. |
| 2007/0270892 A1 | 11/2007 | Makower |
| 2007/0276293 A1 | 11/2007 | Gertner |
| 2007/0276432 A1 | 11/2007 | Stock |
| 2008/0015501 A1 | 1/2008 | Gertner |
| 2008/0051823 A1 | 2/2008 | Makower et al. |
| 2008/0051824 A1 | 2/2008 | Gertner |
| 2008/0051850 A1 | 2/2008 | Sparks et al. |
| 2008/0058710 A1 | 3/2008 | Wilk |
| 2008/0071306 A1 | 3/2008 | Gertner et al. |
| 2008/0086082 A1 | 4/2008 | Brooks |
| 2008/0091237 A1 | 4/2008 | Schwartz et al. |
| 2008/0109027 A1 | 5/2008 | Chen et al. |
| 2008/0147002 A1 | 6/2008 | Gertner |
| 2008/0161717 A1 | 7/2008 | Gertner |
| 2008/0167519 A1 | 7/2008 | St-Germain |
| 2008/0167647 A1 | 7/2008 | Gertner |
| 2008/0167648 A1 | 7/2008 | Gertner |
| 2008/0172074 A1 | 7/2008 | Baker et al. |
| 2008/0172079 A1 | 7/2008 | Birk |
| 2008/0208240 A1 | 8/2008 | Paz |

FOREIGN PATENT DOCUMENTS

| | | |
|---|---|---|
| EP | 1 520 563 | 4/2005 |
| EP | 1 602 392 A1 | 7/2005 |
| EP | 1 591 140 A1 | 11/2005 |
| EP | 1 547 642 B1 | 8/2007 |
| EP | 1 607 071 B1 | 8/2007 |
| EP | 1 670 361 B1 | 4/2008 |
| FR | 2 907 665 | 2/2008 |
| WO | WO 87/00034 | 1/1987 |
| WO | WO/9925418 | 5/1999 |
| WO | WO 9925418 | 5/1999 |
| WO | WO 0009049 | 2/2000 |
| WO | WO 0018330 | 4/2000 |
| WO | WO 00/74573 A1 | 12/2000 |
| WO | WO 0147435 | 7/2001 |
| WO | WO 02/35980 | 5/2002 |
| WO | WO 02071951 | 9/2002 |
| WO | WO 03/055420 | 7/2003 |
| WO | WO 03095015 | 11/2003 |
| WO | WO 2004004542 | 1/2004 |
| WO | WO 2004014237 | 2/2004 |
| WO | WO 2004019765 | 3/2004 |
| WO | WO 2004021894 | 3/2004 |
| WO | WO 2004037064 | 5/2004 |
| WO | WO 2005007232 | 1/2005 |
| WO | WO 2005009288 | 2/2005 |
| WO | WO 2005/018417 A2 | 3/2005 |
| WO | WO 2005/018417 A3 | 3/2005 |
| WO | WO 2005/094447 A2 | 10/2005 |
| WO | WO 2006020370 | 2/2006 |
| WO | WO 2006/049725 A2 | 5/2006 |
| WO | WO 2006063593 A2 | 6/2006 |
| WO | WO 2006108203 | 10/2006 |
| WO | WO 2007017880 A2 | 2/2007 |
| WO | WO 2007/067206 A2 | 6/2007 |
| WO | WO 2007110866 | 10/2007 |
| WO | WO 2008006084 | 1/2008 |
| WO | WO 2008013814 | 1/2008 |

OTHER PUBLICATIONS

Deitel, M., "Overview of Obesity Surgery," *World J. Surg.*, vol. 22, pp. 913-918 (1998).

DeMaria, E.J., "Laparoscopic Adjustable Silicone Gastric Banding," *Surg. Clinics of North America*, vol. 81(5), pp. 1129-1144 (2001).

Doherty, C., "Vertical Banded Gastroplasty," *Surg. Clinics of North America*, vol. 81(5), pp. 1097-1112 (2001).

Marceau, P. et al., "Malabsorptive Obesity Surgery," *Surg. Clinics of North America*, vol. 81(5), pp. 1113-1128 (2001).

McMillan, et al., Arthroscopic Knot-tying techniques. pp. 81-95, 2003.

Buchwald—Overview of Bariatric Surgery. Journal of the American College of Surgeons. pp. 367-375, Mar. 2002.

Sharp, et al., The 4-S Modification of the Roeder Knot: How to Tie It. pp. 1004-1006, vol. 90, No. 6, Dec. 1997.

Akira., JP63277063, Japanese and English Abstract, Nov. 15, 1988, pp. 1-4.

Abhyankar et al, Use of a tissue expander and a polyglactic acid (Vicryl) mesh to reduce radiation enteritis: case report and literature view, 21: pp. 755-757, Aug. 2005.

Buchwald, Overview of Bariatric Surgery, vol. 194, No. 3, Mar. 2002, pp. 367-375.

Burnett, et al., The Use of a Pelvic Displacement Prosthesis to Exclude the Small Intestine from the Radiation Field Following Radical Hysterectomy, 79, pp. 438-443, 2000. http://www.idealibrary.com.

Cheng, Splenic Epidermoid Cyst, pp. 1-3, 1997.

Doherty, Cornelius., Technique of Vertical Banded Gastroplasty. vol. 81, No. 5, Oct. 2001, pp. 1097-1111.

Foglia et al., Management of giant omphalocele with rapid creation of abdominal domain, 41, pp. 704-709, 2006.

Fried et al., Physical Principles of Available Adjustable Gastric Bands: How they Work. Obesity Surgery, 14, 2004, pp. 1118-1122.

Geliebter et al; Extra-abdominal pressure alters food intake, intragastric pressure, and gastric emptying rate. 1986, pp. R549-R552.

Hoffman et al., Morbidity after Intraperitoneal Insertion of Saline-Filled Tissue Expanders for Small Bowel Exclusion from Radiotherapy Treatment Fields: A Prospective Four Year Experience with 34 Patients, pp. 473-483, No. 7, vol. 60, Jul. 1994.

Hainaux et al., Laparoscopic adjustable silicone gastric banding: radiological appearances of a new surgical treatment for morbid obesity. 1999, Abdom Imaging 24: 533-537.

Konturek et al., Neuro-Hormonal Control of Food Intake; Basic Mechanisms and Clinical Implications, 2005, 56, Supp 6, 5-25. www.jpp.krakow.pl.

Lam et al., Huge Splenic Epidemoid Cyst: A Case Report, 1997; 60:113-6.

Lee et al., Laparoscopic Vertical Sleeve Gastrectomy: A Novel Bariatric Procedure—superior to Estabilished Operations? pp. 1-27. 90th Annual Clinical Congress, New Orleans, LA, Oct. 10, 2004.

Malassagne, et al., Intra-abdominal Sengstaken-Blakemore tube Placement for acute venous outflow obstruction in reduced-size Liver, Nov. 1996, 83, pp. 1086.

Mera, et al., Use of the Breast Implant for Liver Graft Malposition. vol. 5, No. 6, Nov. 1999, pp. 534-535.

Obesity Surgery Including Laparoscopy and Allied Care. vol. 16, No. 1, Jan. 2006, pp. 1-2. www.obesitysurgey.com.

Pomerri et al., Adjustable Silicone Gastric Banding of Obesity. , 1992, Gastrointest Radiol 17:207-210.

Schauer, et al., New applications for endoscopy: the emerging field of endoluminal and transgastric bariatric surgery, DOI:10.1007/s00464-006-9008-8, 2006.

The Sleeve Gastrectomy (or 2-Stage Procedure). 2006, pp. 1-2. http://surgicallyslim.com/sleeve.htm.

Walker, et al. Bladder Augmentation in Dogs Using the Tissue Capsule Formed Around a Perivesical tissue Expander, vol. 168, pp. 1534-1536, 2002.

Zwart et al., Gastric Motility: Comparison of Assessement with Real-Time MR Imaging or Barostat Experience1., 224: pp. 592-597, Aug. 2002.

About the Vertical Sleeve Gastrectomy. Mar. 24, 2006, pp. 1-1. http://obesityhelp.com/forums/VSG/about.html.

Gertner MD, Stomach Restriction with an Extragastric Balloon, pp. 1, Abstract for 2007.

Laparoscopic Duodenal Switch, Mar. 24, 2006, http://wo-pub2.med.cornell.edu/chi.bin/WebObjects/PublicA.woa/5/w... p. 1-1.

Med-4840, Product Profile , Mar. 30, 2007, pp. 1-2.

Tucker, Diana, Medical Device Daily. vol. 10, No. 102, pp. 1-10, May 26, 2006.

Trumble et al., "Method for measuring long-term function of muscle-powered implants via radiotelemetry" J. Appl. Physiol. 2001,90: pp. 1977-1985.

Buchwald et al., "Evolution of Operative Procedures for the Management of Morbid Obesity 1950-2000", Obesity Surgery 2002, 12:705-717.

Cummings et al., "Genetics and Pathophysiology of Human Obesity", An Annual Review of Medicine, 2003, 54:453-471.

Johnston et al., The MagenstJohnston et al., "The Magenstrasse and Mill Operation for Morbid Obesity", Obesity Surgery 2003, 13:10-16.

Smith et al., "Modification of the Gastric Partitioning Operation for Morbid Obesity", Am. J. Surgery 142, Dec. 1981.pp. 725-730.

Smith et al., "Results and Complications of Gastric Partitioning: Four Years Follow-Up of 300 Morbidly Obese Patients", The American Journal of Surgery, 1983, (146) pp. 815-819.

* cited by examiner

COMPRESSIVE DEVICE FOR PERCUTANEOUS TREATMENT OF OBESITY

This is the United States national stage of International Application PCT/US04/24612, filed 30 Jul. 2004, which claims the priority filing date of U.S. provisional application 60/494,698, filed 13 Aug. 2003 under 35 U.S.C. §119(e).

TECHNICAL FIELD

This invention pertains to multiple expandable devices that can be implanted to treat obesity in mammals by reducing the volume of the stomach.

BACKGROUND ART

Obesity is a complex, medical disease affecting more than 30% of the population in the United States. Obesity affects an individual's personal quality of life and contributes significantly to morbidity and mortality. Obese patients, i.e. individuals having a body mass index ("BMI") greater than 30, often have a high risk of associated health problems (e.g., diabetes, hypertension, and respiratory insufficiency), including early death. In the United States, approximately 280,000 deaths annually are attributed to obesity and obesity-related diseases. In the case of morbid obesity, studies have shown that conservative treatment with diet and exercise may be ineffective for reducing excess body weight. In addition, specific diets, medications, behavioral modifications, and exercise programs have over a 95% failure rate in morbidly obese individuals. Consequently, surgery is often the most effective means of treatment. "Bariatric surgery" is the field of surgery that treats people who are so overweight that they are suffering health consequences due to the excess weight. The surgery usually involves operations on the stomach to restrict one's ability to eat, or on the small intestine to restrict the absorption of ingested food. See M. Deitel, "Overview of Obesity Surgery," World J. Surg., vol. 22, pp. 913-918 (1998).

A successful bariatric surgery results in a maintained weight loss of greater than 50% of excess body weight and in an increase in patient wellness. An important factor for success is a long-term relationship between the patient and a medical team, which includes the doctor performing the procedure, a dietitian, a psychologist, and a physical therapist. While current bariatric surgery may assist patients in reducing food intake, it may also increase medical risks due to complications inherently associated with surgery, including complications of anesthesia, surgical procedure, wound infections, dehiscence, stomal stenosis, marginal ulcers, thrombophlebitis, and pulmonary problems.

There are several bariatric surgical procedures for treating morbid obesity. One procedure for treating morbid obesity is referred to as a "biliopancreatic diversion." Biliopancreatic diversion surgery is a reduction of the stomach volume and a diversion of food from the stomach to the final segment of the small intestine, bypassing the beginning and middle portions of the small intestine to limit the amount of nutrients and calories absorbed by the body. This procedure removes about one half of the stomach, and then connects the stomach to the last 250 cm of the small intestine. Disadvantages of this surgery include patients suffering from protein malnutrition, anemia, gastric retention, diarrhea, abdominal bloating, and intestinal obstruction. See P. Marceau, et al, "Malabsorptive Obesity Surgery," Surg. Clinics of North America, vol. 81(5), pp. 1113-28 (2001).

Another bariatric surgery, "gastric bypass," is a bypass connecting the lower compartment of the stomach to the initial portion of the small intestine. This procedure limits the amount of food that can be ingested at one sitting and reduces absorption of food across the small intestine. In addition to surgical complications, patients may also suffer from acute gastric dilation, anastomotic leak, anemia, and dumping syndrome. See R. E. Brolin, "Gastric Bypass," Surg. Clinics of North America, vol. 81(5), pp. 1077-1096 (2001).

A third bariatric surgical procedure is "gastric banding," which constricts the stomach to form an hourglass shape. This procedure restricts the amount of food that passes from one section to the next, which induces a feeling of satiety. A band is placed around the stomach near the junction of the stomach and esophagus. The small upper stomach pouch is filled quickly, and slowly empties through the narrow outlet to produce a feeling of satiety. In addition to surgical complications, patients undergoing this procedure may also suffer from esophageal injury, splenic injury, band slippage, staple line disruption, reservoir deflation/leak, and persistent vomiting. See E. J. DeMaria, "Laparoscopic Adjustable Silicone Gastric Banding," Surg. Clinics of North America," vol. 81(5), pp. 1129-44 (2001).

A fourth bariatric surgical procedure is "vertical-banded gastroplasty," which restricts the volume of the stomach by using staples. In this procedure, staples are placed in the upper stomach region to create a small pouch with a narrow outlet to the remaining portion of the stomach. A lap-band is placed around the narrow outlet to provide support and inhibit stretching of the stomach. In addition to surgical complications, patients undergoing this procedure may suffer from vomiting, ulcers, band erosion, and leaks. See C. Doherty, "Vertical Banded Gastroplasty," Surg. Clinics of North America, vol. 81(5), pp. 1097-1112 (2001).

U.S. Pat. No. 6,102,922 describes a device and surgical method for reducing the food intake of a patient by forming a restriction in the stomach using a band. In one embodiment, the band is looped around the esophagus and a portion of the stomach is pulled up through the band loop. This forms a small stomach pouch and a narrow outlet to the remaining portion of the stomach. This allows for a quick filling of the small stomach pouch, and a slow emptying of the stomach through the narrow outlet to produce a feeling of satiety.

U.S. Pat. No. 6,475,136 describes a device for treating heartburn and reflux disease by restricting the amount of food flowing into a stomach or an esophagus, comprising a restriction device (a sphincter or a cuff) that can be adjusted. In one embodiment, the restriction device performs like an artificial sphincter that opens and closes the food passageway in the stomach. In an alternative embodiment, the restriction device comprises an adjustable cuff, a clamp, or a roller to bend or rotate the esophagus or stomach to close or almost close the junction between the stomach and esophagus.

U.S. Pat. No. 4,246,893 describes a device and method for treating obesity by compressing the stomach and reducing its capacity using a single adjustable distensible device (e.g., a balloon) whose volume can be adjusted from an external port.

U.S. Pat. No. 5,993,473 and WO 99/2418 describe a device and surgical method for treating obesity by decreasing the volume of the stomach by using a single expandable device placed inside the stomach cavity.

U.S. Pat. No. 4,694,827 describes a device and method for controlling obesity by deterring ingestion of food using a single balloon that is placed inside the stomach.

U.S. Publication No. 2002/0188354 describes a device for treating obesity by inserting an hourglass-shaped device into the junction between the stomach and the small bowel, which delays gastric emptying of food.

U.S. Pat. No. 6,511,490 describes a device for the treatment of morbid obesity by restricting food passage in the stomach by placing an inflatable band around the stomach to create a pouch with a small opening adjacent to the esophagus. The inflatable band is secured and then inflated until the appropriate sized opening is achieved.

DISCLOSURE OF INVENTION

We have discovered an apparatus and method for effectively treating morbid obesity in mammals, while minimizing the health risks associated with traditional surgery. The device reduces the gastric volume of the stomach and induces early satiety. The "gastric reduction assembly" comprises at least two or more expandable devices (e.g., balloons), each able to be independently inflated and adjusted from an external port. Each expandable device can be filled with a fluid (e.g., CO2, isotonic dextrose solution, isotonic saline solution, etc.) using a filling tube (e.g., a catheter), which can be easily accessed externally. In a preferred embodiment, the gastric reduction assembly is inserted percutaneously through the antero-lateral abdominal wall, and placed at a location exterior to the stomach body, avoiding an abdominal incision. Laparoscopic guidance, optionally, may be used to assist in placing the gastric reduction assembly near the stomach body. Once positioned near the stomach body, the gastric reduction assembly can be inflated to compress the volume of the stomach and effectively limit food intake. The gastric reduction assembly, with multiple expandable devices, minimizes the potential for post-implantation movement. The expandable devices have a size and shape to complement each other, such that they form a barrier when inflated that minimizes post implantation movement.

To further minimize inferior migration, a subcutaneous anchor (e.g., a balloon or ring placed within the fatty layer between the skin and the abdominal wall), may be attached to the filling tubes to anchor the expandable devices to the abdominal wall. In addition, each expandable device may use an intragastric anchor (e.g., a collapsible fixation disc) to anchor the expandable device against the stomach body.

Figure 1:
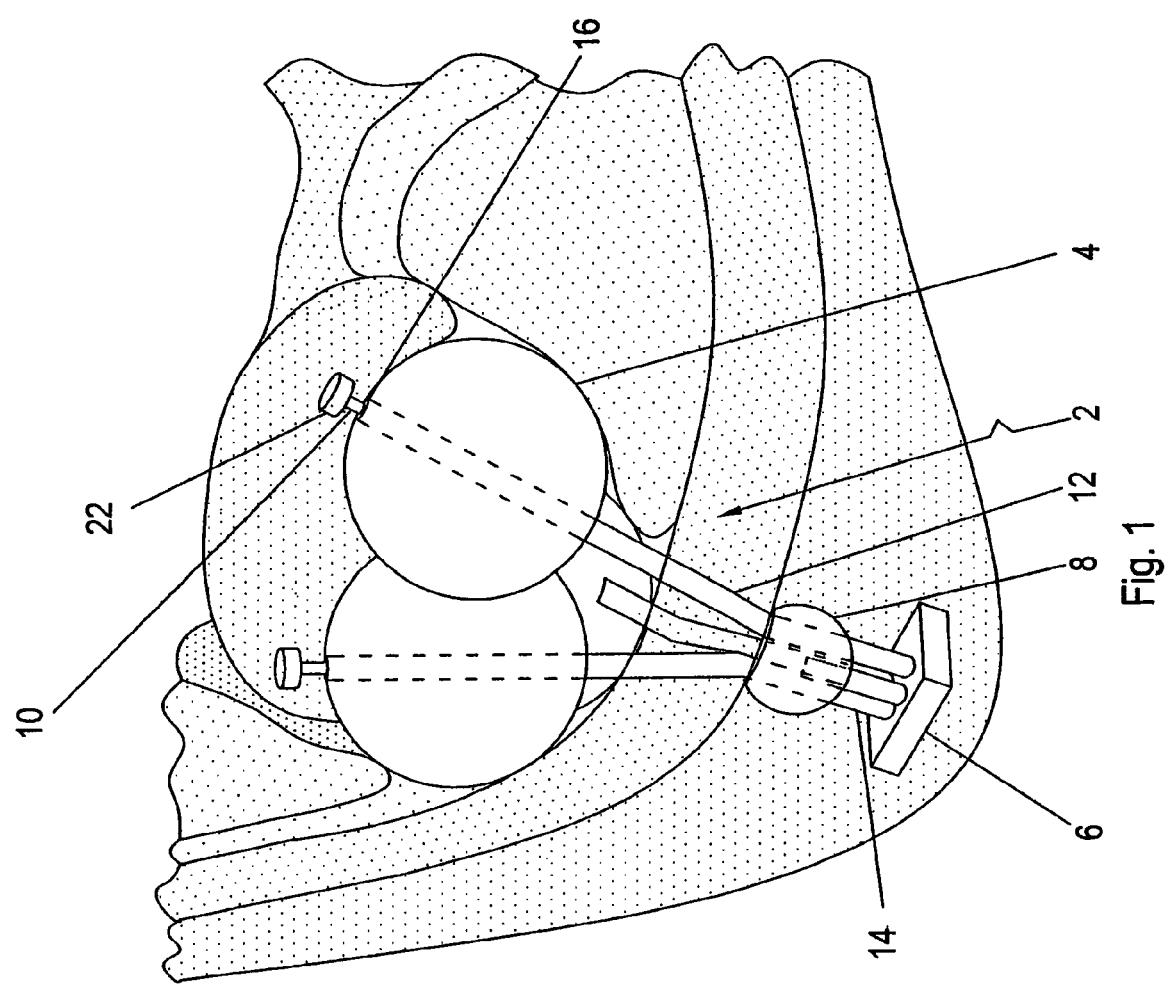
FIG. 1 illustrates a perspective view of one embodiment of the gastric reduction assembly, implanted in the peritoneal cavity around the stomach.

The invention provides a reliable, inexpensive method for treating obesity in mammals by reducing the volume of the stomach without abdominal surgery, thus reducing postoperative surgical complications. The gastric reduction assembly can provide either an intraperitoneal or an extraperitoneal method to compress the stomach. The placement depends on the surgeon's preference, and the physical condition and body habitus of the patient. In the intraperitoneal cavity, expandable devices can be placed either at apregastric location (i.e., either anterior or anterolateral to the stomach) or a retrogastric location (i.e., either posterior or posterolateral to the stomach), or both. In the extraperitoneal cavity, the expandable devices can be placed in any of the anatomical compartments, spaces, or layers of the abdominal wall. Candidates for this minimally invasive procedure include patients with a BMI greater than 40, or patients with a BMI less than 40 and a debilitating disease related to the obesity such as diabetes, hypertension, and respiratory insufficiency.

MODES FOR CARRYING OUT THE INVENTION

The basic design comprises a gastric reduction assembly having at least two or more expandable devices (e.g., balloons), each able to be adjusted and independently inflated. Each device can be inflated with a fluid (e.g., $CO_2$, isotonic dextrose solution, isotonic saline solution, etc.) using a filling tube. The filling tube is accessed externally by way of an access device. To inflate each expandable device, the inlet of each filling tube is attached to a corresponding port, and fluid is injected into the inlet via a carrier (e.g., a hypodermic syringe). Fluid flows through the filling tube into each expandable device. Alternatively, fluid can be removed by reversing the process. The filling tubes may be locked together inside a single catheter or other large tubing such that only one tube crosses the abdominal wall to the access port.

In a preferred embodiment, compression of the stomach is achieved using two or more spherical-shaped expandable devices to form a compressive barrier that reduces the volume of the stomach and minimizes post-implantation movement. Optionally, at least one crescent-shaped expandable device may be used to support the spherical-shaped expandable devices. The shape of the barrier formed by the multiple expandable devices may be adjusted to complement that of surrounding tissues and organs of the patient by changing the volume of the devices.

To further minimize post-implantation movement, a subcutaneous anchor may be used to help anchor the expandable devices to the abdominal wall. In one embodiment, the subcutaneous anchor is a balloon-like device adapted to circumscribe the filling tubes subcutaneously or below the abdominal wall, at the muscular layer level. The volume of the subcutaneous anchor is adjusted by adding fluid. Alternatively, a ring lock may be placed around each filling tube at the muscular layer. In another embodiment, the expandable devices may be anchored to the stomach using an anchor e.g., a collapsible, fixation disc placed inside the stomach. One method of placement is to pass the intragastric anchor through a separate tube that crosses the expandable device and ends inside the stomach cavity. The tube can be accessed externally.

The expandable devices can be implanted bypassing through the skin and across the anterior abdominal wall via a larger tube to a predetermined implantation site. The expandable devices remain at the site, attached to filling tubes that can be accessed externally through a small single access port.

The gastric reduction assembly has several advantages. First, the potential for incisional hernia and wound infections is substantially reduced, since no surgical incision of the abdominal wall is needed. The expandable devices are inserted through the skin and across the anterior abdominal wall via a small puncture. The access device for refilling or deflating the expandable devices is placed in the fatty layers of the abdomen, between the skin and the anterior abdominal muscles. Second, post-implantation movement is substantially reduced, almost eliminating a need to re-orient the expandable devices following implantation. Third, modifications (e.g., inflation, deflation, reorientation, or removal) may easily be done without surgery.

FIG. 1 illustrates a perspective view of one embodiment of the gastric reduction assembly 2, in accordance with the present invention. In this embodiment, the device comprises an access device 6, a subcutaneous anchor 8, and at least two or more expandable devices 4, each having an intragastric anchor 10 and a filling tube 12. Multiple expandable devices 4 are sized and shaped to complement each other such that when inflated, they cluster to form a compressive barrier capable of reducing the stomach volume and minimizing post-implantation movement. To adjustably inflate the expandable devices 4 in the peritoneal cavity, fluid is injected into each filling tube 12 of each expandable device 4 via the access device 6.

Figure 2:
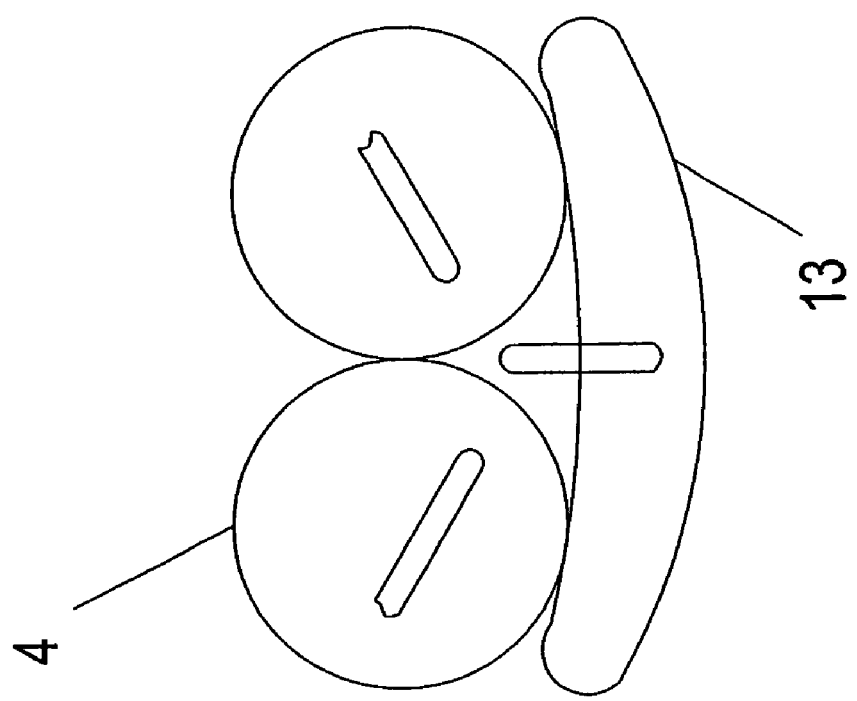
FIG. 2 illustrates a front view of one embodiment of the gastric reduction assembly which has three expandable devices: two spherical-shaped and one crescent-shaped.

As shown in FIG. 1, gastric reduction assembly 2 comprises three spherical-shaped expandable devices 4 (e.g., balloons) placed at a pregastric location. Alternatively, gastric reduction assembly 2 may comprise another number of expandable devices 4 (e.g., two, four, five, six, etc.). Optionally, at least one crescent-shaped expandable device 13 may be used, as shown in FIG. 2. This enhances the compressive barrier by forming a carrier ridge to support spherical-shaped expandable devices 4. Expandable devices 4 can be made of any durable, distensible biocompatible material, such as rubber, latex, or polyurethane elastomer.

As shown in FIG. 1, each filling tube 12 has an inlet at the access device 6 and an outlet to the interior of each expandable device 4 to allow for inflation with fluid. In an alternative embodiment, a single filling tube 12 that has an inlet and outlet (not shown) for each expandable device 4 may be used. Filling tubes 12 should be made of a durable, flexible, biocompatible material, such as TYGON® tubing, polyurethane, or other plastics.

As shown in FIG. 1, subcutaneous anchor 8 is a distensible balloon-like device that circumscribes filling tubes 12 within the fatty layer between the skin and abdominal wall or at a subperitoneal (i.e., below the abdominal wall) region to anchor the expandable devices 4 to the abdominal wall. The balloon-like device is inflated via its own filling tube 14. Alternatively, subcutaneous anchor 8 can be a ring lock (not shown) that joins all filling tubes 12. When the ring lock is placed around filling tubes 12 and advanced towards the abdominal wall, it forms an anchor against the muscular layer of the abdominal wall. Subcutaneous anchor 8 should be made of a durable, distensible biocompatible material, such as rubber, latex, or polyurethane elastomer.

As shown in FIG. 1, intragastric anchor 10 is a collapsible, fixation disc which can be inserted through the stomach wall via tube 12 with a second channel 16 that extends through each expandable device 4. The disc, once opened in the stomach, anchors expandable device 4 against the stomach. Once intragastric anchor 10 is positioned within the stomach and unfolds, an attached suture may be pulled to form a snug fit between the exterior surface of the stomach body and expandable devices 4. The size and shape of intragastric anchor 10 is chosen to complement the inner surface of the stomach, and to provide a sufficient surface area (when unfolded) to prevent intragastric anchor 10 from dislodging from the stomach when tension is applied. Intragastric anchor 10 should be made of a biocompatible material capable of shape memory, e.g., nitinol coated with polytetrafluoroethylene.

An access device 6 comprises ports (not shown) to filling tubes 12. The size and shape of access device 6 is adapted to allow for a tight seal with filling tubes 12 and a fluid carrier (e.g., a hypodermic syringe). The number of ports is determined by the number of tubes (12 and 14) that need to be accessed from the outside.

A preferred method of implanting the gastric reduction assembly is to go though the skin with a minimally invasive puncture. For example, a nasogastric tube (Bard, Covington, Ga.) is inserted into the stomach. The stomach is then inflated to better visualize it under fluoroscopy so that the proper location for an access site through the skin can be determined. The access site should be below the rib cage, near the gastric chamber. Once the access site is determined, a micropuncture needle (e.g., 22 g; Cook, Inc., Bloomington, Ind.) is inserted into the peritoneal cavity immediately in front of the anterior gastric wall. A microwire (e.g., 0.018 in; Cook, Inc., Bloomington, Ind.) is passed through the needle under fluoroscopic guidance and into the peritoneal cavity. Once the microwire reaches the peritoneal cavity, the micropuncture needle is removed over the wire.

Figure 3:
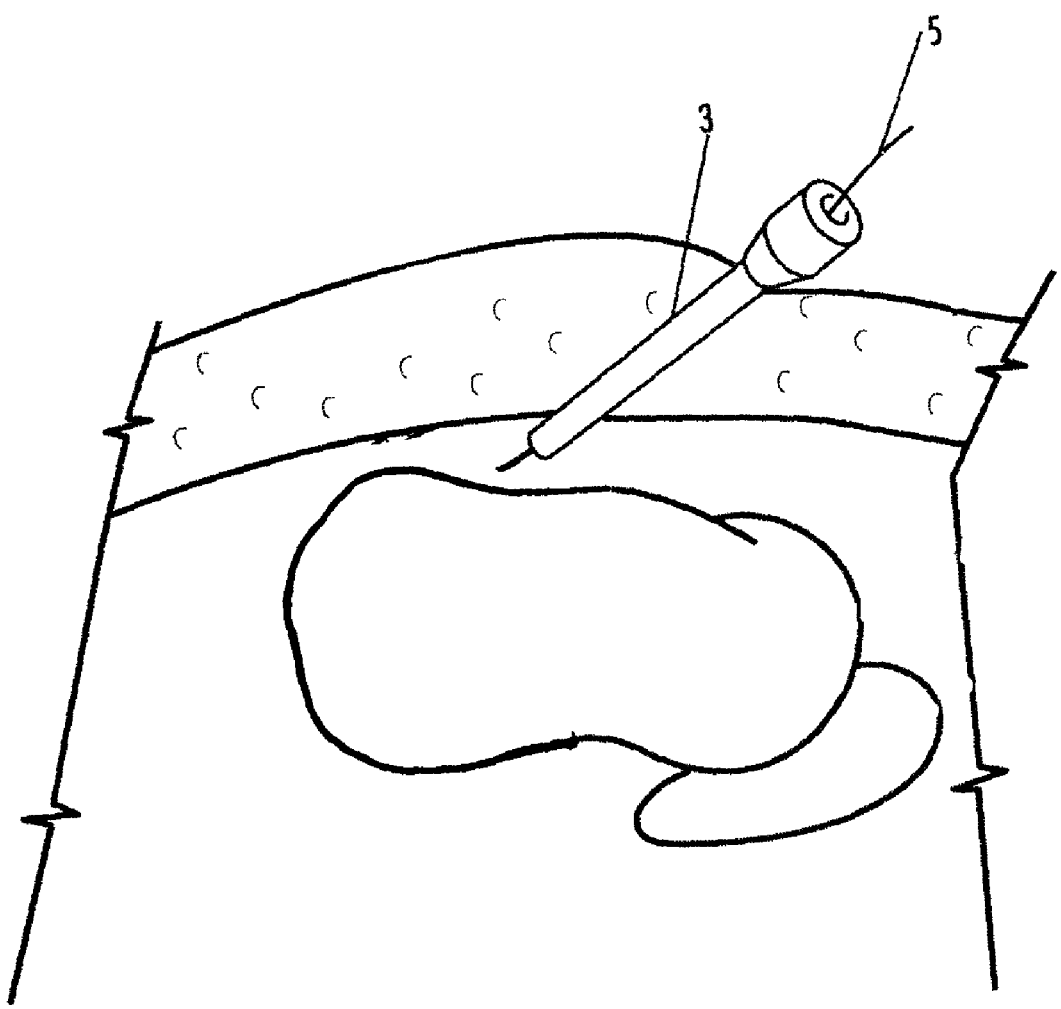
FIG. 3 illustrates a guidewire having been inserted through a sheath according to an embodiment of the present invention described herein.

An access sheath (e.g., 6 French introducer; Cook, Inc., Bloomington, Ind.), a hollow tube that fits through the skin to form a temporary pathway to the peritoneal cavity, is then inserted over the microwire. The microwire is then removed, leaving the access sheath in place. A guidewire 5 (see FIG. 3) (e.g., 0.035 in stiff regular or hydrophilic; Boston Scientific, Natick, Mass.) is then inserted through the access sheath 3 to provide additional support. The opening in the abdominal wall is progressively dilated with dilators (Cook, Inc. Bloomington, Ind.) from 6-14 French. When the opening is sufficiently large, a larger access sheath (e.g., 14 Fr peel-away sheath; Cook, Inc. Bloomington, Ind.) is placed over the 0.035 in stiff guidewire, and the dilator and guidewire are removed. Air is then evacuated from the stomach through the nasogastric tube to provide space for the gastric compression assembly 2.

Introducer tubes (e.g., catheters) containing expandable devices 4 (e.g., balloons) attached to filling tubes 12 are inserted through the access sheath to a predetermined position near the stomach. Expandable devices 4 are released from the introducer tubes. The expandable devices 4 are then partially inflated sequentially near the stomach using a syringe to introduce fluid (e.g., $CO_2$, isotonic saline solution, or isotonic dextrose solution) to the expandable devices 4 through the filling tubes 12. Introducer tubes are slowly withdrawn, and each filling tube 12 is pulled until each partially inflated expandable device 4 contacts the abdominal wall. The access sheath is then removed, and a subcutaneous anchor 8 (e.g., a balloon or ring lock) is placed within the fatty layer between the skin and abdominal wall or the subperitoneal region (i.e., below the abdominal wall) to anchor expandable devices 4. Expandable devices 4 are then inflated to a volume sufficient to compress the stomach, and filling tubes 12 cut to an appropriate length. The inlets to filling tubes 12 are then attached to the ports of access device 6, and access device 6 is placed within the fatty layer between the skin and abdominal wall. The skin is then closed with sutures.

In an alternative embodiment, each expandable device 4 is individually introduced to a preselected stomach compression site near the stomach and then anchored to the stomach, as described below. In this embodiment, filling tube 12 to each expandable device 4 has at least two channels. Filing tube 12 is positioned to pass through expandable device 4 and abut the side of expandable device 4 that is near the stomach. One channel of filling tube 12 has an opening that allows fluid to flow into expandable device 4 to inflate the device. The second channel of filling tube 12 passes intact through expandable device 4 to the wall near the stomach. This channel allows an intragastric anchor 10 to be placed inside the stomach to help anchor expandable device 4 as described below. Initially, a needle (e.g., an 18-gauge needle; Cook, Inc. Bloomington, Ind.) is passed through the access sheath to puncture the stomach wall. A contrast medium (e.g. gastrograffin) is then injected into the stomach to determine the needle's location. Once the location is determined, a suture 22 is attached to intragastric anchor 10, and the collapsed anchor is advanced through the needle into the stomach in a collapsed form using a stiff guidewire (e.g., 0.035 cm guidewire; Boston Scientific Corp, Natick, Mass.). Upon exiting the needle outlet within the stomach, intragastric anchor 10 resumes its disc-shaped configuration. Intragastric anchor 10 can be covered with a biocompatible material (e.g., GORTEX®, DACRON®, polyethylene or silicone) to help seal the gastric puncture site. The 18-gauge needle is then removed, while the stiff guidewire and suture remain attached to the intragastric anchor 10. Preferably, suture 22 is attached to the guidewire to allow for withdrawal. This process is repeated for each of the remaining expandable devices 4. The stiff guidewire is then passed through the second channel of filling tube 12 for each expandable device 4. Expandable devices 4 are then positioned at preselected stomach compression sites as described above. After verifying the compressive effects of each expandable device 4 on the gastric volume of the stomach, the stiff guidewires are disconnected from sutures 22 and removed. Each suture 22 is then pulled back through the second channel of filling tube 12 to anchor the device to the stomach wall. The access sheath is then removed, and filling tubes 12 are cut to an appropriate length. The ends of each suture are pulled through the second channel and attached to access device 6 to anchor expandable devices 4. Expandable devices 4 can then be inflated or deflated through access device 6, as necessary. Access device 6 is then placed within the fatty layer between the skin and the abdominal wall, and the skin is closed with sutures.

Clinical trials will initially involve testing two groups (a test and a control) of pigs weighing more than 50 kg. The gastric reduction assembly will be implanted into the test group. Once the gastric reduction assembly has been implanted, an upper gastrointestinal study ("UGI") will be conducted with barium to check the gastric volume and passage of material through the stomach into the small intestine. The volume of the expandable devices will be adjusted in the test group based on the findings of the UGI. UGIs will be conducted at various intervals to check on the location and volume of the expandable devices. The two groups will be weighed weekly. After six months, the animals will be euthanized and the position of the gastric reduction assembly evaluated during necropsy. The data will be analyzed for differences in weight loss between the two groups.

The complete disclosures of all references cited in this specification are hereby incorporated by reference. In the event of an otherwise irreconcilable conflict, however, the present specification shall control.

We claim:

1. A method of treating obesity in a patient, said method comprising:

making a percutaneous opening to the abdominal cavity of the patient;

passing an expandable device, while in a contracted configuration, through said opening;

positioning the expandable device adjacent the stomach of the patient;

expanding the expandable device to occupy a volume of space and substantially prevent the stomach from expanding into the volume of space; and anchoring the expandable device to at least one structure in the abdominal cavity, wherein the expandable device is drawn into contact with a location of the at least one structure that the expandable device is anchored to.

2. A method of treating a patient, said method comprising:

passing a device including an expandable member in a collapsed configuration through an opening in the skin of the patient, and into the abdominal cavity of the patient;

anchoring at least a portion of the expandable member, relative to at least one structure in the abdominal cavity without piercing the stomach, wherein the at least a portion is drawn into contact with a location of the at least one structure that the at least a portion is anchored to; and expanding the expandable member to an expanded configuration in a space in the abdominal cavity to perform at least one of: prevention of expansion of the stomach of the patient into the space; and compression of a portion of the stomach.

3. The method of claim 2, wherein said method is performed as a percutaneous procedure.

4. The method of claim 2, wherein said method is performed as a laparoscopic procedure.

5. The method of claim 2, wherein a guidewire is passed through the skin of the patient, and into the abdominal cavity, and wherein the device is passed over the guidewire to guide the device to an intended location in the abdominal cavity.

6. The method of claim 2, further comprising inserting a sheath through a minimally invasive opening made through the skin and the abdominal wall, wherein the guidewire is inserted through the sheath to pass the guidewire through the skin and abdominal wall and into the abdominal cavity.

7. The method of claim 2, wherein said device further comprises a second expandable member, said method further comprising at least partially expanding the second expandable member.

8. The method of claim 2, wherein the device is passed in a compact configuration, the compact configuration being achieved and maintained by compacting the expandable member and inserting the expandable member within a sheath.

* * * * *